(12) United States Patent
Ros Fàbrega et al.

(10) Patent No.: US 11,534,191 B2
(45) Date of Patent: Dec. 27, 2022

(54) LOADING DEVICE FOR LOADING A MEDICAL DEVICE INTO A CATHETER

(71) Applicant: ANACONDA BIOMED, SL, Barcelona (ES)

(72) Inventors: Robert Ros Fàbrega, Molins de Rei (ES); Iñaki Galve Murillo, Barcelona (ES); Ofir Arad Hadar, Sant Cugat del Vallès (ES); Ane Lizarazu Gonzalez, Barcelona (ES)

(73) Assignee: Anaconda Biomed, S.L., Sant Cugat del Vallès (ES)

( * ) Notice: Subject to any disclaimer, the term of this patent is extended or adjusted under 35 U.S.C. 154(b) by 0 days.

(21) Appl. No.: 17/415,866

(22) PCT Filed: Dec. 24, 2019

(86) PCT No.: PCT/EP2019/087001
§ 371 (c)(1),
(2) Date: Jun. 18, 2021

(87) PCT Pub. No.: WO2020/144071
PCT Pub. Date: Jul. 16, 2020

(65) Prior Publication Data
US 2022/0079609 A1    Mar. 17, 2022

(30) Foreign Application Priority Data
Jan. 11, 2019   (EP) .................................... 19382015

(51) Int. Cl.
*A61M 39/06*   (2006.01)
*A61B 17/221*   (2006.01)
(Continued)

(52) U.S. Cl.
CPC .. *A61B 17/221* (2013.01); *A61B 2017/00907* (2013.01); *A61B 2017/2215* (2013.01);
(Continued)

(58) Field of Classification Search
CPC .............. A61M 25/01; A61M 25/0105; A61M 25/0113; A61M 25/013; A61M 25/09041;
(Continued)

(56) References Cited

U.S. PATENT DOCUMENTS

| 4,921,478 A | 5/1990 | Solano et al. |
| 5,011,488 A | 4/1991 | Ginsburg |

(Continued)

FOREIGN PATENT DOCUMENTS

| CN | 102973332 A | 3/2013 |
| CN | 104159525 A | 11/2014 |

(Continued)

OTHER PUBLICATIONS

Berkhemer et al.; A randomized trial of intraarterial treatment for acute ischemic stroke; New England Journal of Medicine; 372; pp. 11-20; Jan. 1, 2015.

(Continued)

*Primary Examiner* — Kathleen S Holwerda
*Assistant Examiner* — Kankindi Rwego
(74) *Attorney, Agent, or Firm* — Shay Glenn LLP

(57) ABSTRACT

A loading device for loading a medical device into a catheter is provided. The loading device comprises a body having a lumen to receive an expandable portion of a medical device. The lumen has a length as the expandable portion when the latter is in a collapsed configuration and has a diameter that is greater than the collapsed configuration. The body comprises a first portion and a second portion that are reversibly separable to expose the lumen in an open configuration and enclose the lumen in a closed configuration. The first and second portions each comprise an inner face having a groove defining a first portion of the lumen and a second portion of the lumen, respectively. The body also has a distal tip portion to reversibly couple with a hemostatic valve of a (Continued)

delivery catheter. A method of loading a medical device into a catheter is also provided.

16 Claims, 10 Drawing Sheets

(51) Int. Cl.
    *A61B 17/00*          (2006.01)
    *A61B 17/22*          (2006.01)

(52) U.S. Cl.
    CPC .... *A61B 2017/22079* (2013.01); *A61M 39/06* (2013.01); *A61M 2039/062* (2013.01)

(58) Field of Classification Search
    CPC ........ A61M 2025/09116; A61M 39/06; A61M 39/10; A61M 2039/062; A61F 2/0095; A61F 2/82; A61F 2/958; A61F 2002/9522; A61F 2/9522; A61B 17/221; A61B 2017/0042; A61B 2017/0046; A61B 2017/00469; A61B 2017/00907; A61B 2017/22079; A61B 2017/2215; A61B 5/6852
    USPC ......... 606/108, 194, 195, 198, 200; 623/1.1, 623/1.11, 1.12, 1.2, 1.23
    See application file for complete search history.

(56) References Cited

U.S. PATENT DOCUMENTS

| | | | |
|---|---|---|---|
| 5,102,415 A | 4/1992 | Guenther et al. | |
| 5,190,561 A | 3/1993 | Graber | |
| 5,605,530 A * | 2/1997 | Fischell | A61F 2/95 600/3 |
| 5,769,871 A | 6/1998 | Mers Kelly et al. | |
| 5,908,435 A | 6/1999 | Samuels | |
| 5,971,938 A | 10/1999 | Hart et al. | |
| 6,159,230 A | 12/2000 | Samuels | |
| 6,190,303 B1 * | 2/2001 | Glenn | G21F 5/018 600/3 |
| 6,402,771 B1 | 6/2002 | Palmer et al. | |
| 6,663,650 B2 | 12/2003 | Sepetka et al. | |
| 6,695,858 B1 | 2/2004 | Dubrul et al. | |
| 6,752,819 B1 | 6/2004 | Brady et al. | |
| 7,004,954 B1 | 2/2006 | Voss et al. | |
| 7,108,677 B2 | 9/2006 | Courtney et al. | |
| 7,578,830 B2 | 8/2009 | Kusleika et al. | |
| 7,686,825 B2 | 3/2010 | Hauser et al. | |
| 8,679,142 B2 | 3/2014 | Slee et al. | |
| 8,758,364 B2 | 6/2014 | Eckhouse et al. | |
| 8,784,441 B2 | 7/2014 | Rosenbluth et al. | |
| 8,858,497 B2 | 10/2014 | Di Palma et al. | |
| 8,864,792 B2 | 10/2014 | Eckhouse et al. | |
| 9,005,237 B2 | 4/2015 | Eckhouse et al. | |
| 9,034,008 B2 | 5/2015 | Eckhouse et al. | |
| 9,186,487 B2 | 11/2015 | Dubrul et al. | |
| 9,463,035 B1 | 10/2016 | Greenhalgh et al. | |
| 9,561,121 B2 | 2/2017 | Sudin et al. | |
| 9,585,741 B2 | 3/2017 | Ma | |
| 9,844,381 B2 | 12/2017 | Eckhouse et al. | |
| 9,861,783 B2 | 1/2018 | Garrison et al. | |
| 10,285,720 B2 | 5/2019 | Gilvarry et al. | |
| 11,013,523 B2 | 5/2021 | Jacobi et al. | |
| 2004/0024416 A1 | 2/2004 | Yodfat et al. | |
| 2004/0073243 A1 | 4/2004 | Sepetka et al. | |
| 2004/0098099 A1 | 5/2004 | McCullagh et al. | |
| 2004/0143317 A1 | 7/2004 | Stinson et al. | |
| 2004/0243102 A1 | 12/2004 | Berg et al. | |
| 2004/0260333 A1 | 12/2004 | Dubrul et al. | |
| 2006/0058838 A1 | 3/2006 | Bose et al. | |
| 2006/0064073 A1 | 3/2006 | Schonholz et al. | |
| 2006/0155305 A1 | 7/2006 | Freudenthal et al. | |
| 2007/0213765 A1 | 9/2007 | Adams et al. | |
| 2007/0276332 A1 * | 11/2007 | Bierman | A61M 25/02 604/174 |
| 2009/0163846 A1 | 6/2009 | Aklog et al. | |
| 2009/0198269 A1 | 8/2009 | Hannes et al. | |
| 2010/0030256 A1 | 2/2010 | Dubrul et al. | |
| 2010/0222864 A1 | 9/2010 | Rivelli et al. | |
| 2011/0160763 A1 | 6/2011 | Ferrera et al. | |
| 2011/0213297 A1 | 9/2011 | Aklog et al. | |
| 2012/0065660 A1 | 3/2012 | Ferrera et al. | |
| 2012/0179181 A1 | 7/2012 | Straub et al. | |
| 2013/0261638 A1 | 10/2013 | Diamant et al. | |
| 2013/0325055 A1 | 12/2013 | Eckhouse et al. | |
| 2013/0325056 A1 | 12/2013 | Eckhouse et al. | |
| 2014/0052161 A1 | 2/2014 | Cully et al. | |
| 2014/0074144 A1 | 3/2014 | Shrivastava et al. | |
| 2014/0155908 A1 | 6/2014 | Rosenbluth et al. | |
| 2014/0243885 A1 | 8/2014 | Eckhouse et al. | |
| 2014/0277015 A1 | 9/2014 | Stinis | |
| 2015/0112376 A1 | 4/2015 | Molaei et al. | |
| 2015/0164666 A1 | 6/2015 | Johnson et al. | |
| 2015/0231360 A1 | 8/2015 | Watanabe et al. | |
| 2015/0359547 A1 | 12/2015 | Vale et al. | |
| 2016/0081704 A1 | 3/2016 | Jeon et al. | |
| 2016/0256255 A9 | 9/2016 | Ma | |
| 2017/0105743 A1 | 4/2017 | Vale et al. | |
| 2017/0119408 A1 | 5/2017 | Ma | |
| 2017/0119409 A1 | 5/2017 | Ma | |
| 2017/0215900 A1 | 8/2017 | Lowinger et al. | |
| 2017/0215902 A1 | 8/2017 | Leynov et al. | |
| 2017/0239444 A1 * | 8/2017 | Parker | A61B 5/6852 |
| 2017/0333060 A1 | 11/2017 | Panian | |
| 2018/0028209 A1 | 2/2018 | Sudin et al. | |
| 2018/0064454 A1 | 3/2018 | Losordo et al. | |
| 2018/0126132 A1 | 5/2018 | Heilman et al. | |
| 2018/0132876 A1 | 5/2018 | Zaidat | |
| 2018/0206862 A1 | 7/2018 | Long | |
| 2018/0318062 A1 | 11/2018 | Sudin et al. | |
| 2018/0353196 A1 | 12/2018 | Epstein et al. | |
| 2018/0361114 A1 | 12/2018 | Chou et al. | |
| 2019/0167284 A1 | 6/2019 | Friedman et al. | |
| 2019/0167287 A1 | 6/2019 | Vale et al. | |
| 2019/0216476 A1 | 7/2019 | Barry et al. | |
| 2019/0269425 A1 | 9/2019 | Sudin et al. | |
| 2019/0269491 A1 | 9/2019 | Jalgaonkar et al. | |
| 2019/0274810 A1 | 9/2019 | Phouasalit et al. | |
| 2019/0307471 A1 | 10/2019 | Friedman et al. | |
| 2020/0000613 A1 | 1/2020 | Shrivastava et al. | |
| 2020/0008822 A1 | 1/2020 | Eckhouse et al. | |
| 2020/0085444 A1 | 3/2020 | Vale et al. | |
| 2020/0205838 A1 | 7/2020 | Walzman | |
| 2020/0281612 A1 | 9/2020 | Kelly et al. | |
| 2021/0000582 A1 | 1/2021 | Chomas et al. | |
| 2021/0059695 A1 | 3/2021 | Haran et al. | |
| 2021/0068852 A1 | 3/2021 | Spence | |
| 2021/0077134 A1 | 3/2021 | Vale et al. | |
| 2021/0236150 A1 | 8/2021 | Arad Hadar | |

FOREIGN PATENT DOCUMENTS

| | | |
|---|---|---|
| EP | 2662109 A1 | 11/2013 |
| ES | 2341973 T3 | 6/2010 |
| ES | 2381099 T3 | 5/2012 |
| GB | 2498349 A | 7/2013 |
| JP | 2005500138 A | 1/2005 |
| WO | WO99/45835 A2 | 9/1999 |
| WO | WO02/087677 A2 | 11/2002 |
| WO | WO2004/002564 A1 | 1/2004 |
| WO | WO2005/027751 A1 | 3/2005 |
| WO | WO2008/124567 A1 | 10/2008 |
| WO | WO2008/157202 A1 | 12/2008 |
| WO | WO2009/014723 A1 | 1/2009 |
| WO | WO2011/068924 A1 | 6/2011 |
| WO | WO2011/082319 A1 | 7/2011 |
| WO | WO2012/156924 A1 | 11/2012 |
| WO | WO2012/158269 A1 | 11/2012 |
| WO | WO2013/008233 A1 | 1/2013 |
| WO | WO2013/152327 A1 | 10/2013 |
| WO | WO2014/008460 A2 | 1/2014 |
| WO | WO2014/127389 A2 | 8/2014 |

(56) References Cited

FOREIGN PATENT DOCUMENTS

| WO | WO2014/204860 A1 | 12/2014 |
|---|---|---|
| WO | WO2015/006782 A1 | 1/2015 |
| WO | WO2015/189354 A1 | 12/2015 |
| WO | WO2016/113047 A1 | 7/2016 |
| WO | WO2017/072663 A1 | 5/2017 |
| WO | WO2017/074290 A1 | 5/2017 |
| WO | WO2017/075544 A1 | 5/2017 |
| WO | WO2018/080590 A1 | 5/2018 |
| WO | WO2018/160966 A1 | 9/2018 |
| WO | WO2019/064306 A1 | 4/2019 |
| WO | WO2019/178131 A1 | 9/2019 |
| WO | WO2020/021333 A2 | 1/2020 |
| WO | WO2020/079082 A1 | 4/2020 |
| WO | WO2020/099386 A1 | 5/2020 |
| WO | WO2021/016213 A1 | 1/2021 |

OTHER PUBLICATIONS

Ceretrieve; 3 pages; retrieved from the internet (http://trendlines.com/portfolio/ceretrieve/) on Sep. 13, 2018.

Duffy et al.; Novel methodology to replicate clot analogs with diverse composition in acute ischemic stroke; Journal of neurointerventional surgery; 9(5); pp. 486-491; May 1, 2017.

Fennell et al.; What to do about fibrin rich "tough clots"? Comparing the Solitaire stent retriever with a novel geometric clot extractor in an in vitro stroke model; Journal of neurointerventional surgery; 10(9); pp. 907-910; Sep. 1, 2018.

Mokin et al.; Stent retriever thrombectomy with the Cover accessory device versus proximal protection with a balloon guide catheter: in vitro stroke model comparison; Journal of neurointerventional surgery; 8(4); pp. 413-417; Apr. 1, 2016.

Cortinas Villazon et al.; U.S. Appl. No. 17/274,973 entitled "A device and a thrombectomy apparatus for extraction of thrombus from a blood vessel," filed Mar. 10, 2021.

Arad Hadar et al.; U.S. Appl. No. 17/291,696 entitled "A thrombectomy system and methods of extracting a thrombus from a thrombus site in a blood vessel of a patient," filed May 6, 2021.

Arad et al.; U.S. Appl. No. 62/760,786 entitled "Thrombectomy system comprising an expandable tip aspiration catheter and clot-capture element," filed Nov. 13, 2018.

Bouthillier et al.; Segments of the internal carotid artery: a new classification; Neurosurgery; 38(3); pp. 425-433; Mar. 1, 1996.

Salmon et al.; U.S. Appl. No. 17/500,844 entitled "Thrombectomy system and method of use," filed Oct. 13, 2021.

Rios Garriga et al.; U.S. Appl. No. 17/621,717 entitled "Delivery catheter device and system for accessing the intracranial vasculature," filed Dec. 22, 2021.

\* cited by examiner

LOADING DEVICE FOR LOADING A MEDICAL DEVICE INTO A CATHETER

TECHNICAL FIELD OF THE INVENTION

The present invention relates generally to medical devices. More in particular, the invention relates to a loading device for loading a medical device into a catheter. The invention also relates to a method of loading a medical device into a catheter.

BACKGROUND OF THE INVENTION

Endovascular treatment has been employed in cases of stroke since the 1990s. The number of patients it has been used on has grown slowly but steadily. Recently, the first positive randomized study was published (Berkhemer O. A. et al. "A randomized trial of intraarterial treatment for acute ischemic stroke." N Engl J Med. January 2015; 372: 1 1-20. doi: 10.1056/NEJMoa141 1587. Epub 17 Dec. 2014. PubMed PMID: 25517348) demonstrating the efficacy of the thrombectomy treatment as compared to more conventional medical treatments by reducing the disability rate three months after a stroke. In addition, four other major similar clinical trials were published in 2015 definitively confirming the superiority of thrombectomy treatment with latest-generation devices by reducing impairment as compared to other medical treatments.

With regard to endovascular treatment, initially the strategy was local perfusion of a fibrinolytic agent through a microcatheter directly into the thrombus. In the early 2000s, a new device was introduced that appeared to be more effective than intraarterial fibrinolysis. It was a spiral that opened around the thrombus, facilitating its extraction (MERCi®). In 2006, a system basically based on bringing a large-gauge catheter in close proximity to the thrombus in order to aspirate it became popular. The catheter is connected to a continuous aspiration pump (Penumbra®). This system has evolved over the years, seeking to attain a catheter with an increasingly large diameter, able to navigate close to the thrombus.

The use of the so-called stent retrievers began around 2009. Their use consists of crossing the thrombus with a microcatheter, then advancing the stent through the microcatheter. Once the distal end of the sheathed device has reached the most distal part of the thrombus, the stent is unsheathed, self-expanding at the thrombus level and capturing the thrombus. It is advisable to wait several minutes with the stent expanded within the thrombus to increase its engagement with the thrombus. The expanded stent is then withdrawn, dragging the thrombus with it. This final step can be done while aspirating through the catheter to try to reverse the flow and thus increase the chances of recovering the thrombus. Stent retrievers have entirely displaced the first-generation devices described above due to their high efficacy, ease to use and reduced procedure times.

In addition, when using a stent retriever, a guide balloon catheter is often used. When treating clots in cerebral vessels, this catheter only advances to the extracranial carotid (distant from thrombi located in the intracranial arteries). Upon inflation of the balloon situated at the end of the catheter, the catheter is able to stop the flow in the arterial segment distal to the balloon, which is where the thrombus to be extracted is located. By aspirating through the catheter, the flow in the arterial segment distal to the balloon can be reversed in order to facilitate the removal of the thrombus together with the stent retriever.

In summary, there are currently two trends in the use of thrombectomy devices: on one hand the so-called stent retrievers (with or without balloon catheter), and on the other hand devices based on an aspiration catheter (with manual aspiration with syringe or automatic aspiration with aspiration pump). The two techniques can be combined.

An expandable stent (such as a stent retriever) needs to be collapsed in order to load it into a delivery catheter. Therefore, it would be desirable to provide a device and method for facilitating loading of the expandable stent into a delivery catheter in a simple and reliable manner.

SUMMARY OF THE INVENTION

The present invention relates generally to a loading device for loading a medical device into a catheter. For example, the loading device can be used to load a funnel of an aspiration catheter into the lumen of a delivery catheter.

One aspect of the invention provides a loading device for loading into a catheter a medical device having a nonexpandable portion and an expandable portion with an expanded configuration and a collapsed configuration. In some embodiments, the loading device includes a body having a lumen configured to receive the expandable portion of the medical device, the lumen having a length at least as long as the expandable portion of the medical device when the expandable portion is in the collapsed configuration, the lumen having a diameter that is greater than the collapsed configuration of the medical device, the body comprising a first portion and a second portion that are reversibly separable to expose the lumen in an open configuration and enclose the lumen in a closed configuration, the first portion comprising an inner face, and the second portion comprising an inner face, wherein the inner face of the first portion has a first groove that defines a first portion of the lumen and the inner face of the second portion has a second groove that defines a second portion of the lumen, wherein the body has a distal tip portion that is sized, shaped, and configured to reversibly couple with a hemostatic valve (i.e. a valve allowing the passage of medical devices simultaneously with infusion of drugs or contrast media into the vascular system) of the catheter such that the lumen of the loading device is aligned with a lumen of the catheter when the distal tip is coupled with the hemostatic valve of the catheter, wherein the lumen of the loading device extends through the distal tip portion.

In some embodiments of the loading device, the distal tip portion is formed from the first portion and the second portion, wherein the distal tip portion in the closed configuration comprises a cylindrical wall portion and a central tubular member, and wherein the lumen extends through the central tubular member.

In some embodiments, the lumen has a substantially constant diameter and/or the lumen may be straight.

In some embodiments, the distal tip portion has a length that is sufficient to extend at least partially within the hemostatic valve. In some embodiments, the distal tip portion has a length that is sufficient to extend past a sealing mechanism in the hemostatic valve.

In some embodiments, the first groove defines half of the lumen and the second groove defines the other half of the lumen. In other embodiments, the first groove defines approximately three quarters of the lumen and the second groove defines approximately one quarter of the lumen.

Some embodiments also include a plurality of alignment features disposed around the first groove and extending from the inner face of the first portion and a plurality of receptacles on the inner face of the second portion that are configured to receive the plurality of alignment features when the inner face of the first portion abuts against the inner face of the second portion, wherein the alignment features around the first groove each has a receiving surface configured to guide the nonexpandable portion of the medical device into the first groove. Some such embodiments also include a plurality of alignment features disposed around the second groove and extending from the inner face of second portion and a plurality of receptacles on the inner face of the first portion that are configured to receive the plurality of alignment features around the second groove when the inner face of the second portion abuts against the inner face of the first portion, wherein the alignment features around the second groove each has a receiving surface configured to guide the nonexpandable portion of the medical device into the second groove.

In some embodiments, the receiving surfaces of the alignment features are sloped downwards towards the first groove.

In some embodiments, the body is made of a translucent or clear material. Some embodiments may also include a hinge connecting the first portion to the second portion.

In some embodiments, the first portion has a first tab that extends from the first portion and the second portion has a second tab that extends from the second portion, wherein the first tab and the second tab are proximate each other when the first portion and the second portion are in the closed configuration. Some such embodiments also have a third tab located between about 30 degrees to 120 degrees away from the first tab and a fourth tab located between about 30 degrees to 120 degrees away from the second tab.

Another aspect of the invention provides a method of loading into a catheter a medical device having a nonexpandable portion and an expandable portion with an expanded configuration and a collapsed configuration. The method includes the steps of: positioning the nonexpandable portion into a first groove of a first portion of a loader body, wherein the loader body is in an open configuration that exposes the first groove on the first portion of the loader body and a second groove on a second portion of the loader body; closing the loader body around the nonexpandable portion of the medical device such that the second groove is aligned with the first groove to form a lumen that encloses the nonexpandable portion of the medical device while the expandable portion of the medical device remains outside the loader body; retracting the expandable portion of the medical device into the lumen of the closed loader body such that the expandable portion adopts the collapsed configuration within the lumen; placing a distal end of the loader body against a hemostatic valve located at a proximal end of the catheter; advancing the expandable portion of the medical device past the hemostatic valve and into the catheter; retracting the loader body from the hemostatic valve; opening the loader body; and removing the loader body from the medical device.

Some embodiments of the method also include the step of inserting the distal end of the loader body into the hemostatic valve. In some such embodiments, the distal end of the loader body is not inserted past a sealing mechanism within the hemostatic valve. In other such embodiments, the distal end of the loader body is inserted past a sealing mechanism within the hemostatic valve.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

6A is a side cross-sectional view of another embodiment of a loading device for loading a thrombectomy device into a delivery catheter.

Figure 6A:
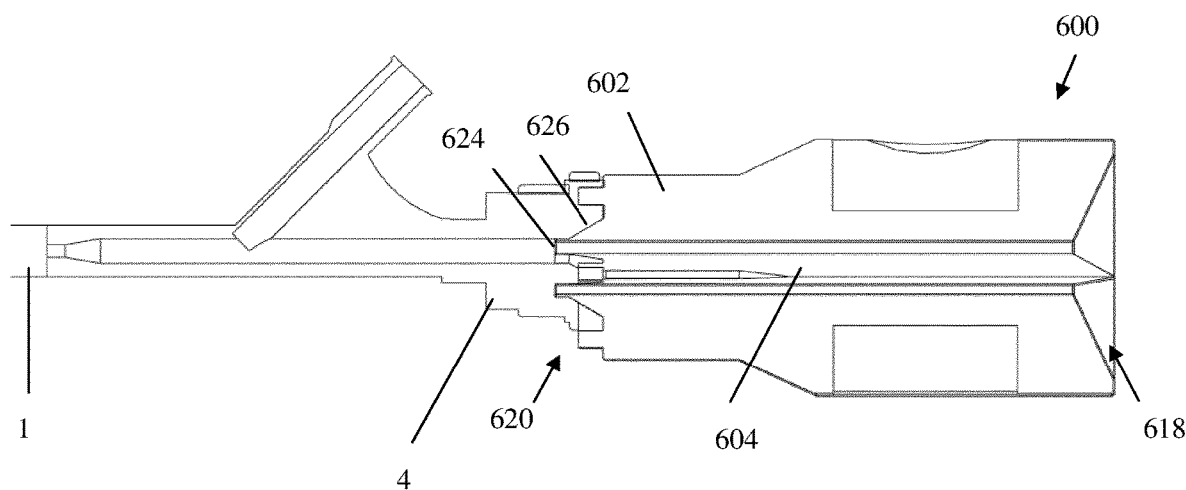
Figure 6B:
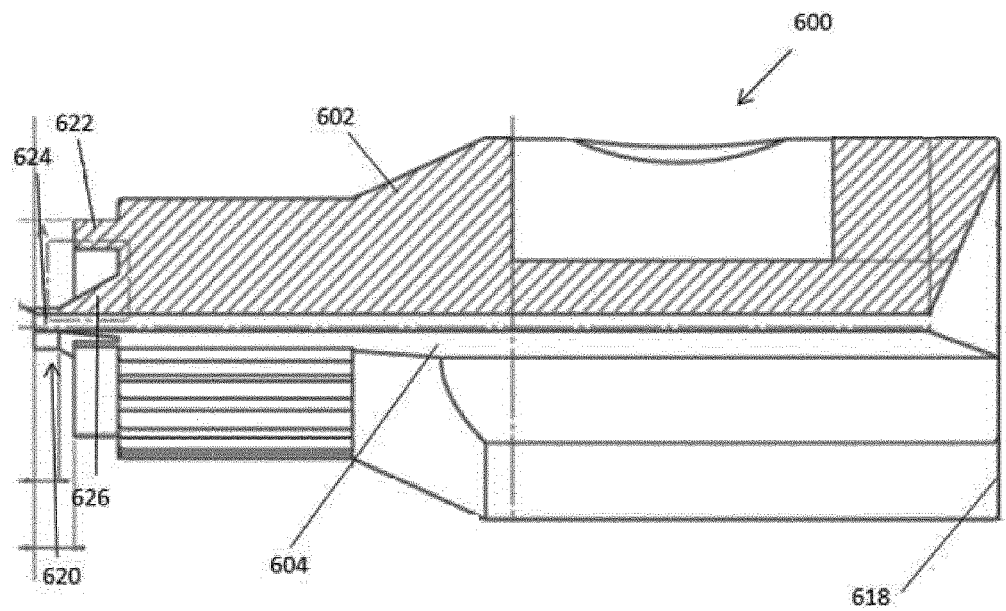

FIG. 6B is a side cross-sectional view of the loading device of FIG. 6A.

Figure 6C:
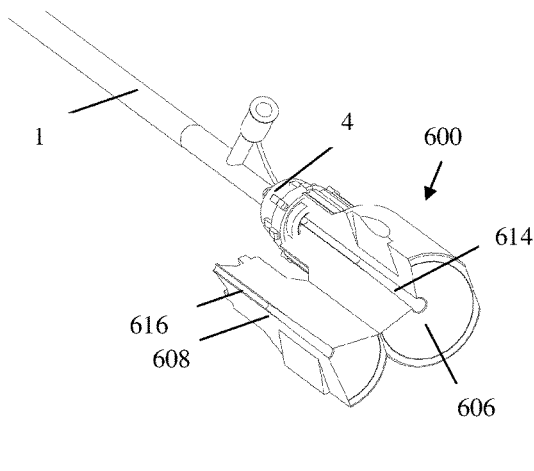

FIG. 6C is a perspective view of the delivery catheter and loading device of FIG. 6A with the loading device in an open configuration.

Figure 6D:
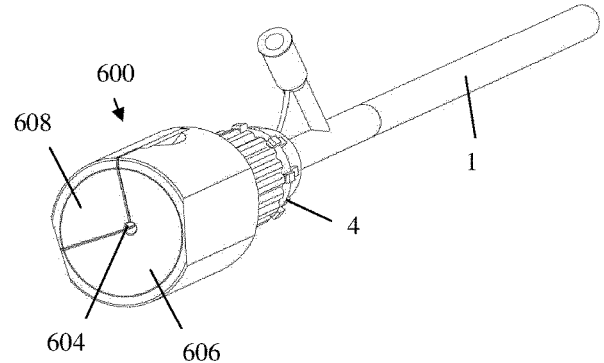

FIG. 6D is a perspective view of the delivery catheter and loading device of FIG. 6A with the loading device in a closed configuration.

Figure 6E:
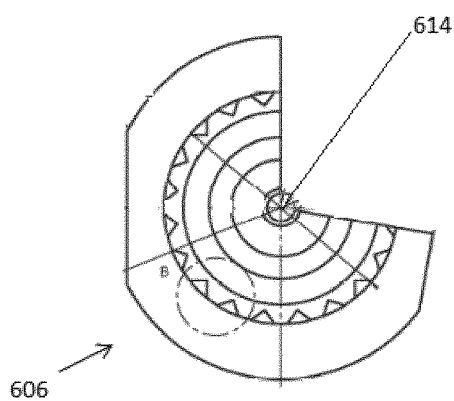

FIG. 6E is a cross-sectional view of first portion of the loading device of FIG. 6A.

Figure 6F:
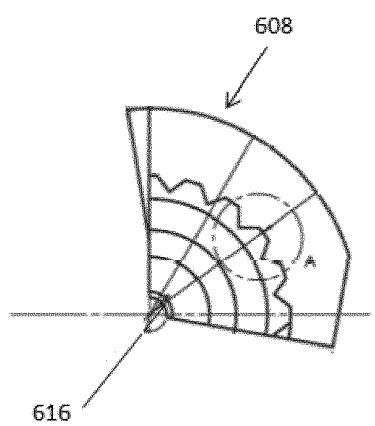

FIG. 6F is a cross-sectional view of a second portion of the loading device of FIG. 6A.

Figure 7A:
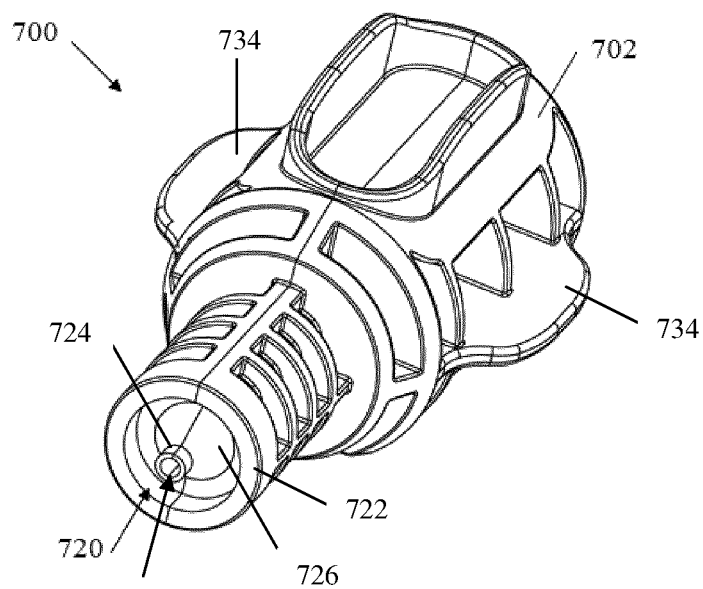

FIG. 7A is a perspective view of yet another embodiment of a loading device for loading a thrombectomy device into a delivery catheter, with the loading device in a closed configuration.

Figure 7B:
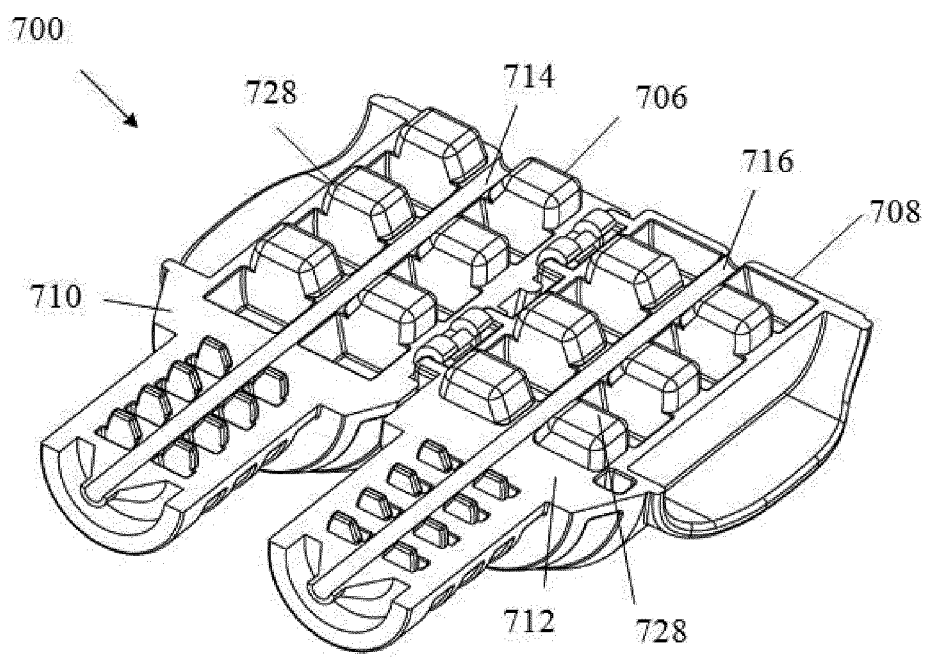

FIG. 7B is a perspective view of the loading device of FIG. 7A in an open configuration.

Figure 7C:
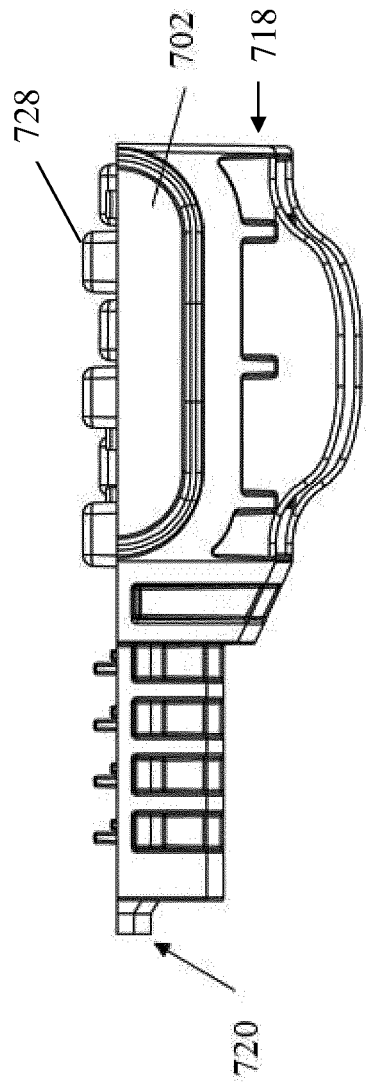

FIG. 7C is a side elevational view of one component of the loading device of FIG. 7A.

DETAILED DESCRIPTION OF THE INVENTION

The loading device according to the present invention may be used, e.g., to load a thrombectomy device designed to remove a thrombus 7 from an intracranial artery 6 without causing or allowing the thrombus 7 to fragment and without causing damage to the intracranial artery 6 thus avoiding development of additional thrombi, such as the device described in U.S. application Ser. No. 15/649,266, published as U.S. 2017/0303949, or the device described in U.S. Application No. 62/760,786, filed Nov. 13, 2018. Though these devices are particularly suited for removal of intracranial artery thrombi, they may be used to remove a thrombus 7 in any artery or vein 6. The loading device of this invention may be used to load other expandable medical devices into catheters as well such as a flow diverter or a balloon-guide catheter.

Figure 1:
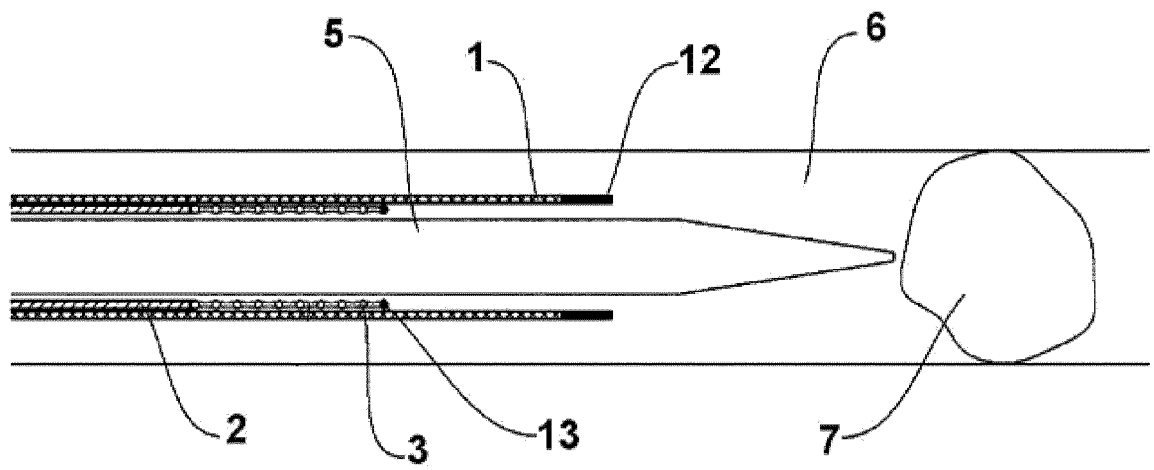
FIG. 1 is a schematic elevational view of the thrombectomy device according to the present invention in its approaching configuration, which is used for clearing the way through blood vessels and reaching the artery where the thrombus is located.
Figure 2:
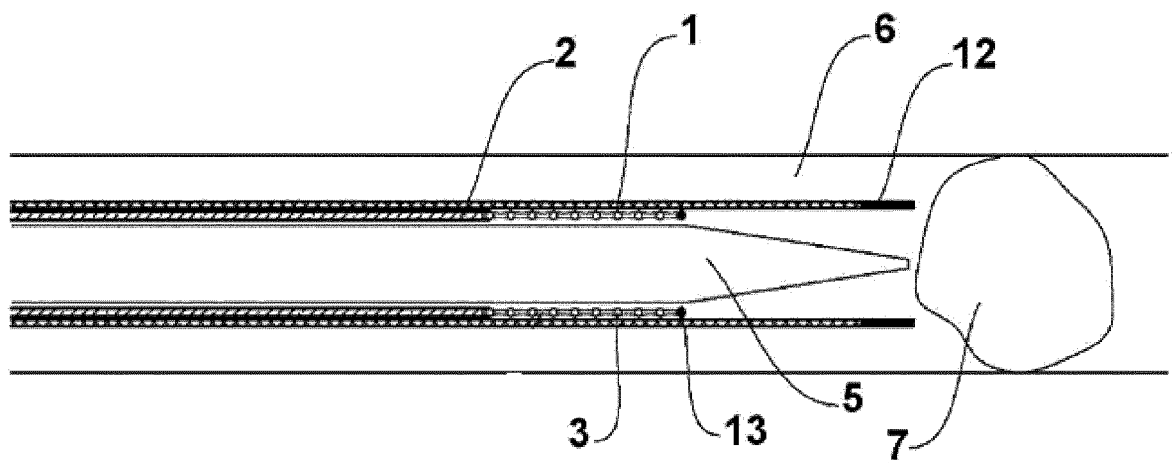
FIG. 2 is a schematic elevational view of the thrombectomy device according to the present invention in its retracted or navigational configuration, used to navigate the delivery catheter (carrying inside it the aspiration funnel catheter) to the face of the thrombus.
Figure 3:
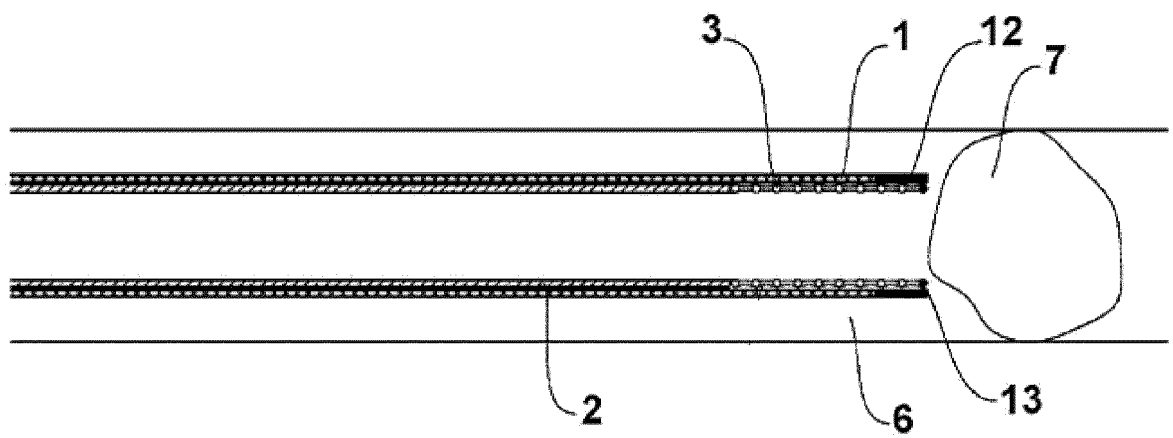
FIG. 3 is a schematic elevational view of the thrombectomy device according to the present invention in its aligned or ready-to-expand configuration, ready to deliver the aspiration funnel.
Figure 4:
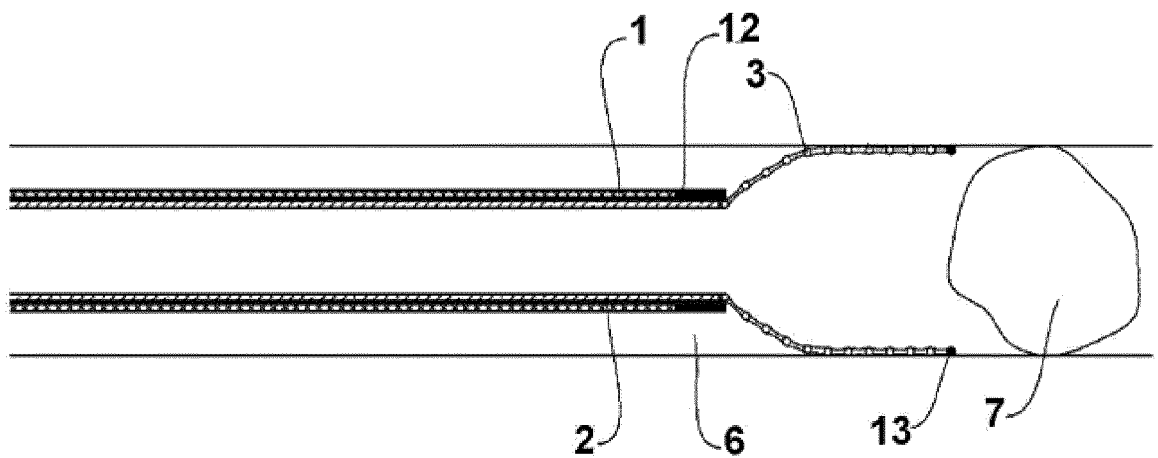
FIG. 4 is a schematic elevational view of the thrombectomy device according to the present invention in its expanded or ready-to-aspirate configuration, when the funnel adapts itself to the vessel shape and faces the thrombus before it is aspirated.

For example, the loading device according to the present invention may be used to load the thrombectomy device shown in FIGS. 1-4. The thrombectomy device of FIGS. 1-4 particularly comprises a tapered dilator catheter 5, an aspiration funnel catheter 2 (comprising an expandable stent 3 and a pusher element, such as an aspiration catheter formed, e.g., from a hypotube) and a delivery catheter 1. As shown in FIGS. 1-4 the thrombectomy device of this embodiment particularly also comprises a radiographic marker 12 to indicate the location of the thrombus 7 in the artery 6 and a radiographic marker 13 to indicate the location of the thrombectomy device in the vascular system. Moreover, as shown in FIGS. 1-3, the thrombectomy device may be advanced through the delivery catheter 1 in a collapsed configuration in which the expandable stent 3 is collapsed (Other aspects of this exemplary device are described in U.S. 2017/0303949). As shown in FIG. 4, when delivery catheter 1 is withdrawn from expandable stent 3, stent 3 expands to its expanded configuration (shown here as a funnel), in which it may contact the vessel wall adjacent the thrombus 7. Aspiration can then be applied to pull the thrombus 7 into the expandable stent 3.

In one embodiment of the present invention, the loading device can be used to load the expandable stent or funnel 3 of such thrombectomy device into the lumen of the delivery catheter 1 in a quick and efficient manner that is easy to use. FIGS. 5A-6F illustrate various embodiments of a loading device. The loading device functions to collapse the expandable stent or funnel 3 in an even and uniform manner so that it can be loaded into the lumen of the delivery catheter 1 in a way that does not interfere with the deployment of the funnel 3 from the delivery catheter 1. In some embodiments, the loading devices described herein can be used to similarly load other types of expandable medical devices into the lumen of a delivery catheter.

FIGS. 5A-5H illustrate one embodiment of a loading device 500 for loading the funnel 3 of a thrombectomy device into a delivery catheter 1. The loading device 500 has a body 502 that encloses a lumen 504 that is sized and shaped to receive the expandable stent or funnel 3 and extend from a proximal end 518 of the body 502 to a distal end 520 of the body 502. In some embodiments, as shown in FIGS. 5A-5H, the lumen 504 can have a diameter that is substantially constant and that is slightly greater (e.g., about 5-25% greater) than the diameter of the aspiration catheter 2 to which the funnel 3 is attached. In some embodiments, the lumen 504 has a diameter between about 2 to 3 mm. In some embodiments the lumen 504 has a diameter less than about 2, 3, 4, and 5 mm. The lumen can be cylindrical and straight and have a length that is at least as long as the funnel 3 in the collapsed configuration. In contrast to a lumen 504 with a tapering diameter that is described below, using a constant diameter lumen can improve the pushability of the collapsed funnel 3 through the loading device 500, while also reducing folding and deformation problems to the funnel 3 that may occur when using a tapering lumen because the constant diameter lumen evenly spreads the radial collapsing force applied by the loading device 500 throughout the entire length of the collapsed funnel 3.

To access the lumen 504, the body 502 can reversibly opened and/or separated into two portions 506, 508 to expose the lumen 504. In some embodiments as shown in FIGS. 5A-5H, the two portions 506, 508 can be two halves of the body 502 that can be joined together at a hinge 509 or joint that facilitates the opening and closing of the two portions of the body 502. In the open configuration, the inner faces 510, 512 of the two portions 506, 508 each have a groove 514, 516 that defines a portion (e.g., a half) of the lumen.

The body 502 of the loading device has the proximal end 518 and the distal end 520 through which the lumen 504 extends. The distal end 520 (from now on referred as distal tip portion) is sized and shaped to reversibly couple with the hemostatic valve 4 of the delivery catheter 1. When the distal tip portion 520 is coupled with the hemostatic valve 4, the lumen 504 of the loading device 500 is aligned with the lumen of the delivery catheter 1 so that the collapsed funnel 3 can be advanced from the loading device 500 and into the lumen of the delivery catheter 1.

Figure 5A:
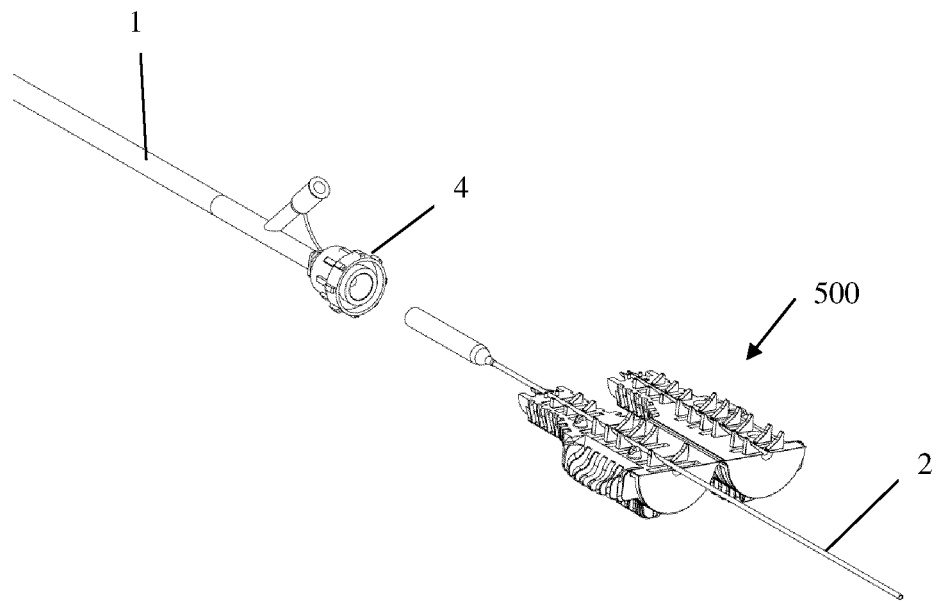
FIG. 5A is a perspective exploded view illustrating one embodiment of a loading device for loading a thrombectomy device into a delivery catheter, with the loading device in an open configuration.
Figure 5B:
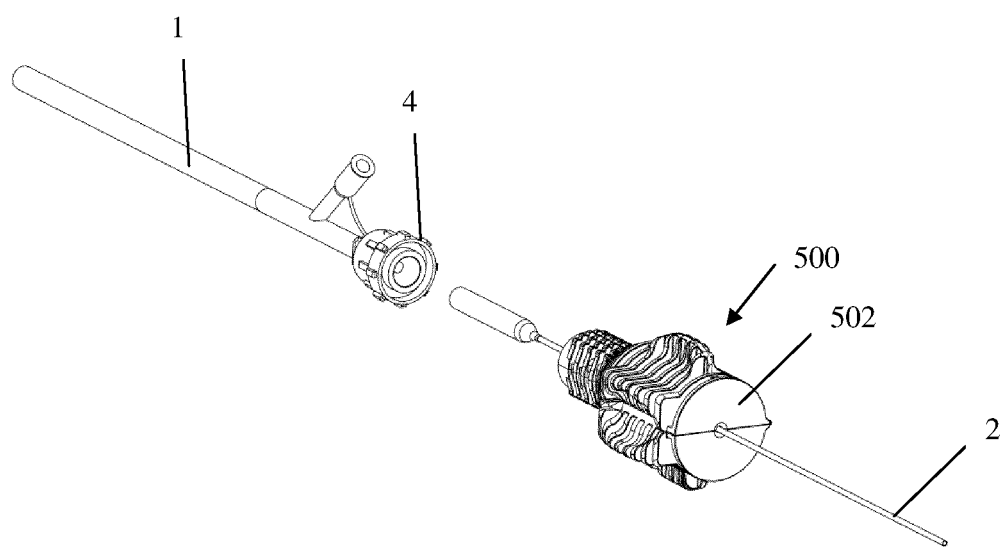
FIG. 5B is a perspective exploded view of the thrombectomy device, the delivery catheter, and the loading device of FIG. 5A in a closed configuration.
Figure 5C:
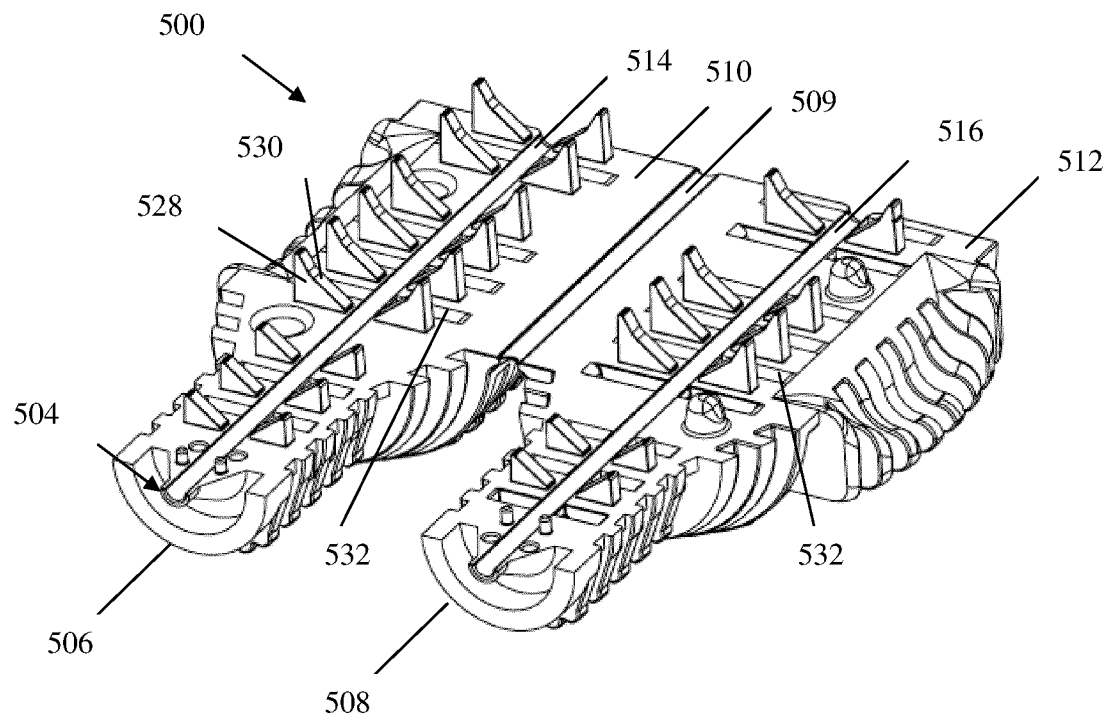
FIG. 5C is a perspective view of the loading device of FIG. 5A in the open configuration.
Figure 5D:
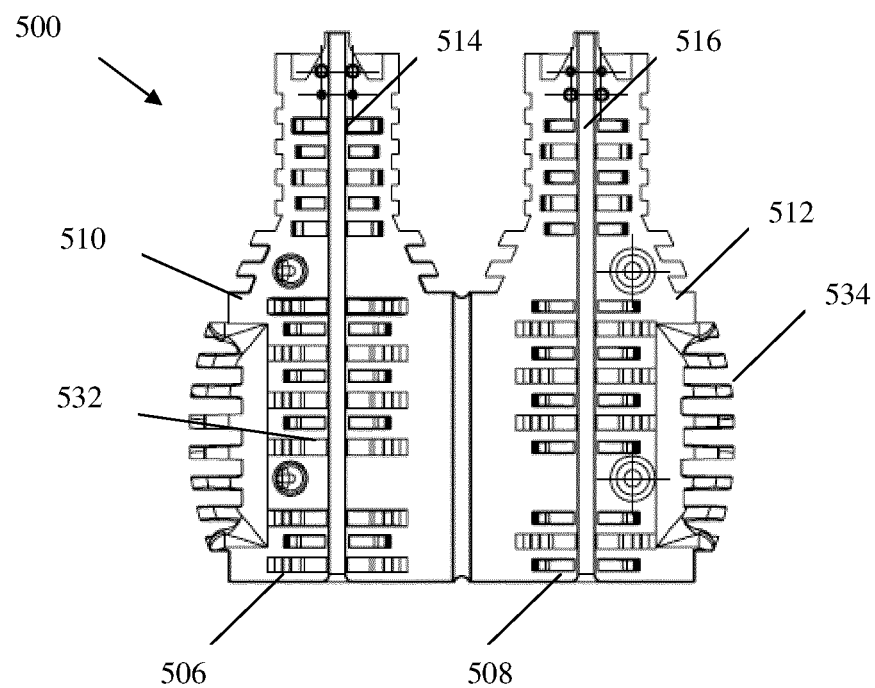
FIG. 5D is a top plan view of the loading device of FIG. 5A in the open configuration.
Figure 5E:
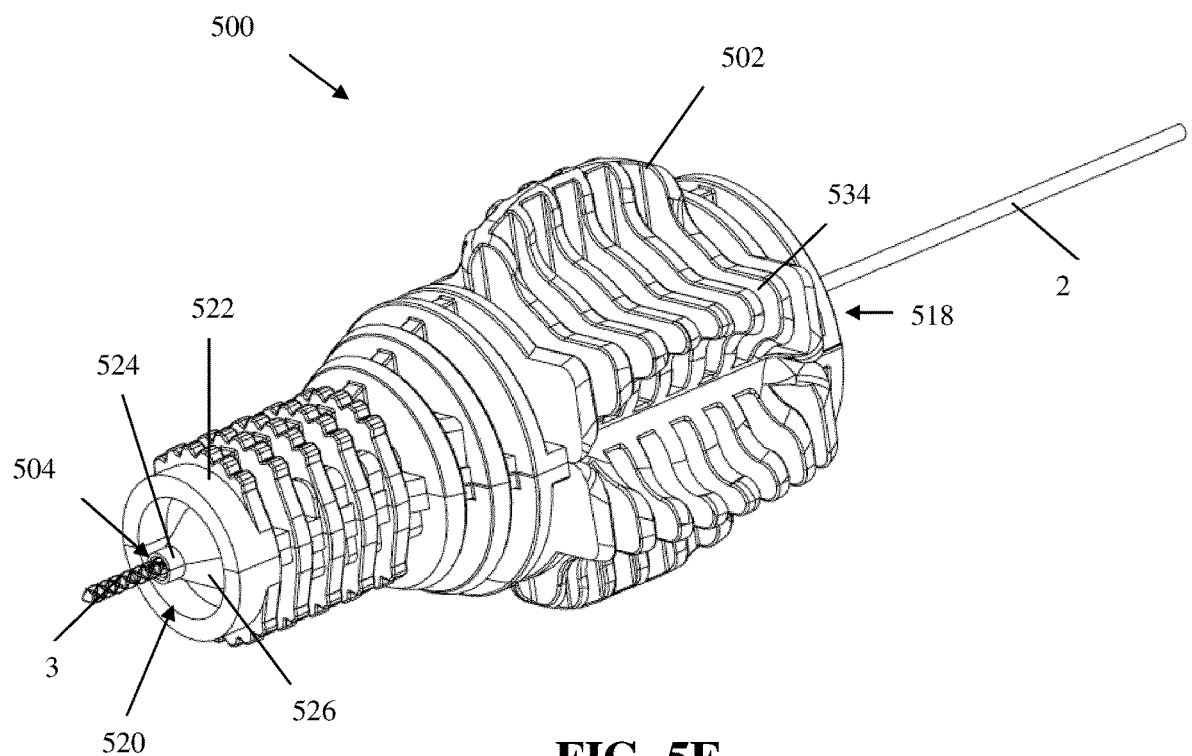
FIG. 5E is a perspective exploded view of the thrombectomy device and the loading device of FIG. 5A in the closed configuration.
Figure 5F:
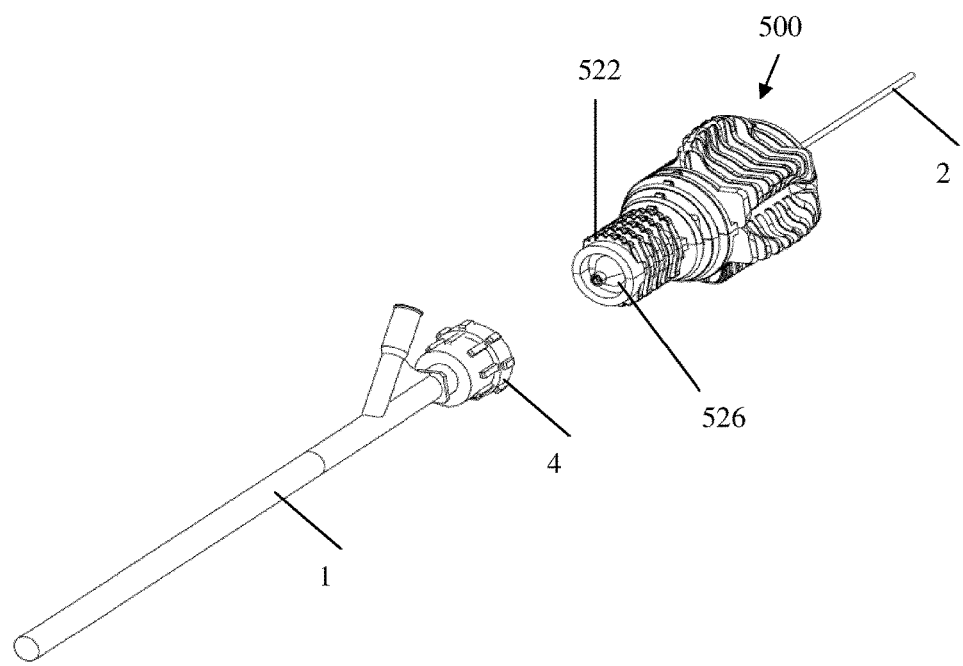
FIG. 5F is a perspective exploded view of the thrombectomy device, the delivery catheter, and the loading device of FIG. 5A in the closed configuration.

In some embodiments, as shown particularly in FIG. 5F, the distal tip portion 520, when in the closed configuration, can have a cylindrical wall portion 522 that surrounds a central tubular member 524 that extends from the distal tip portion 520 from a conical projection 526. As shown, the lumen 504 extends through the central tubular member 524. This shape allows the distal tip portion 520 of the loading device 500 to tightly couple with the hemostatic valve 4 of the delivery catheter 1. In some embodiments, the central tubular member 524 extends at least partially into the lumen of the delivery catheter 1 when the distal tip portion 520 is coupled to the hemostatic valve 4. In some embodiments, the central tubular member 524 extends past the sealing mechanism of the hemostatic valve 4 when the distal tip portion 520 is coupled to the hemostatic valve 4. In other embodiments, the central tubular member 524 abuts against the end of the hemostatic valve 4 when the distal tip portion 520 is coupled to the hemostatic valve 4.

FIGS. 5A, 5C, and 5D illustrate an embodiment of alignment features 528 that can be disposed around one or both grooves 514, 516. Adding alignment features 528 to both grooves 514, 516 allows the user to place the aspiration catheter in either portion 506, 508 when loading the aspiration catheter 2 into the loading device 500. Each alignment feature 528 can extend from the inner face around the groove and can have a sloped surface 530 that tapers towards the groove and that functions to guide the aspiration catheter 2 into the groove. On the opposite inner face(s) are a plurality of receptacles 532 that are sized and shaped to receive the plurality of alignment features 528 so that the two portions 506, 508 can be closed tightly together. The plurality of alignment features 528 and receptacles 532 also function to assist in the proper alignment of the two sections 506, 508 during the closure process, thereby ensuring that the two portions 506, 508 are properly closed together to form the lumen 504 in the closed configuration.

In some embodiments, the body 502 can be made of a translucent or clear material such as a polycarbonate material, among others, so that user can visually confirm that the aspiration catheter 2 and funnel 3 are properly loaded within the loading device 500. In other embodiments, the body 502 can be made of an opaque material.

Figure 5G:
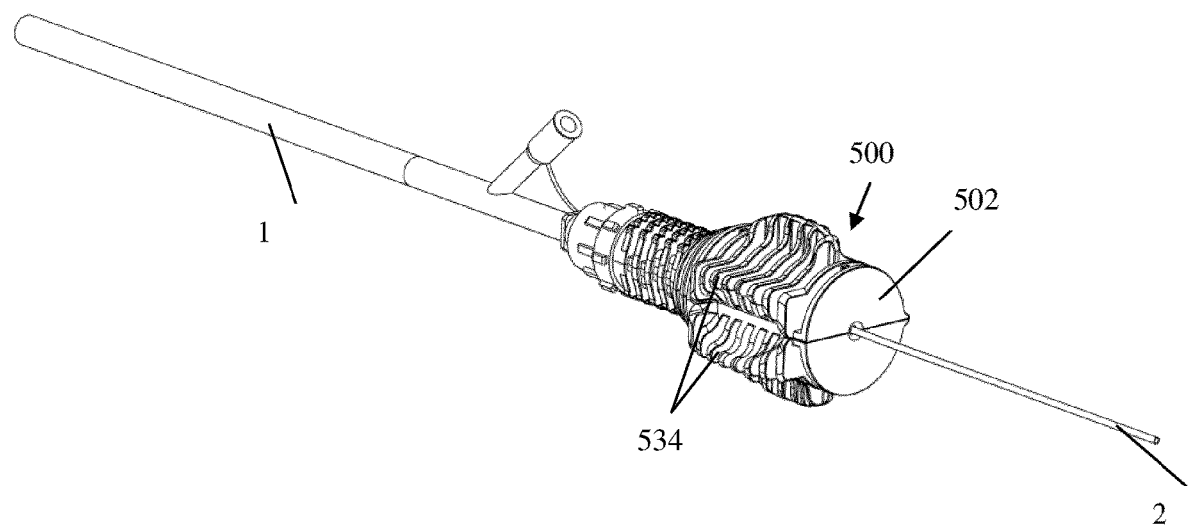
FIG. 5G is a perspective view of the thrombectomy device, the delivery catheter, and the loading device of FIG. 5A in the closed configuration.

In some embodiments, as shown in FIGS. 5B, 5E, and 5G for example, the body 502 can include one or more finger tabs 534 that provide surfaces for the user to press against to open and close the body 502. For example, one tab 534 can extend from the outer surface of each portion 506, 508 near the free edges (i.e., edge opposite the hinge) of each portion 506, 508. When the body 502 is in a closed configuration, the pair of tabs 534 can be adjacent or proximate each other. In some embodiments, the loading device can have additional tabs, such as a third tab located between about 30 degrees to 120 degrees away from the first tab and a fourth tab located between about 30 degrees to 120 degrees away from the second tab.

The loading device of this invention may be used to load the expandable and nonexpendable portions of a thrombectomy device into a catheter. The loading device 500 is opened by gripping the tabs 534 and separating the two portions 506, 508 of the body 502 from each other to expose the two grooves 514, 516 that form the lumen 504. In some embodiments, the loading device 500 may be shipped and provided to the user in an opened configuration or in a closed configuration. As shown in FIG. 5A, the shaft of the aspiration catheter 2 can be placed in one of the grooves 514, 516 that has alignment features 528. In embodiments where both grooves 514, 516 have alignment features 528, the shaft of the aspiration catheter 2 can be placed in either groove 514, 516. The shaft of the aspiration catheter 2 is placed such that the expandable stent or funnel 3 is completely distal the distal tip 520 of the loading device 500. In some embodiments, the shaft of the aspiration catheter 2 can be roughly placed in one of the grooves 514, 516, meaning the shaft only needs to be placed near or proximate the groove, and as long as the shaft is disposed within the bounds of the alignment features 528, the shaft will be guided into the groove when the body 502 is closed.

Once the shaft has been placed in or proximate one of the grooves 514, 516 as described above, the user can close the two portions 506, 508 of the body 502 together, which results in the shaft of the aspiration catheter 2 being enclosed by the lumen 504 of the loading device 500 with the funnel 3 located outside the loading device 500 and distal the distal tip 520, as shown in FIG. 5B. During closing of the body 502, the alignment features 528 guide and help retain the shaft of the aspiration catheter 2 within the grooves. The alignment features 528 also enter and are retained within the receptacles 532.

Particularly, the alignment features 528 are square shaped.

Next, as shown in FIGS. 5E and 5F, the aspiration catheter 2 is retracted in a proximal direction to pull the expandable stent or funnel 3 towards the distal tip 520 of the loading device 500 and into the lumen 504 of the closed body 502. As the funnel 3 is drawn into the lumen 504 of the loading device, the stent or funnel 3 is collapsed into a collapsed configuration within the lumen 504. The aspiration catheter 2 is retracted proximally until the stent or funnel 3 is completely enclosed by the lumen 504 of the loading device 500. The stent or funnel 3 may be longer in its collapsed configuration than in its expanded configuration. Lumen 504 is therefore long enough to accommodate the length of the collapsed stent or funnel 3.

Next, as shown in FIG. 5G, the distal tip 520 of the loading device 500 is placed against the hemostatic valve 4 located at the proximal end of the delivery catheter 1. In some embodiments, the distal tip 520 is reversibly coupled to the hemostatic valve 4. In some embodiments, a portion of the distal tip 520 (e.g., a central tubular member 524 as described above) can be inserted into the hemostatic valve 4 and the lumen of the delivery catheter 1. In some embodiments, a portion of the distal tip 520 (e.g., a central tubular member 524 as described above) can be inserted past the sealing mechanism within the hemostatic valve 4. In other embodiments, the distal tip 520 remains proximal the sealing mechanism of the hemostatic valve 4. The advantage of having the distal tip 520 advance past the sealing mechanism of the hemostatic valve 4 is that it allows the funnel 3 to be advanced into the lumen of the delivery catheter 1 from the loading device 500 at a point that is past the sealing mechanism. In contrast, if the distal tip 520 merely abuts against the proximal end of the hemostatic valve 4 or does not extend past the sealing mechanism, the funnel 3 must be advanced out of the loading device 500 and into the lumen of the delivery catheter 1, and then advanced through the lumen of the delivery catheter 1 past the sealing mechanism of the hemostatic valve 4, which may in some embodiments disrupt the distal end of the collapsed funnel 3 (e.g., cause folding of the distal end of the funnel). In other embodiments, advancing the funnel 3 across the sealing mechanism is not a problem due to the mechanical properties of the funnel 3 and/or the properties of the sealing mechanism. Having at least a portion of the distal tip 520 inserted into the hemostatic valve 4 is beneficial because it aligns and stabilizes the coupling between the aspiration catheter 2 and delivery catheter 1, thereby allowing the user to grasp the delivery catheter 1 in one hand while grasping and pushing the shaft of the aspiration catheter in the other hand.

Figure 5H:
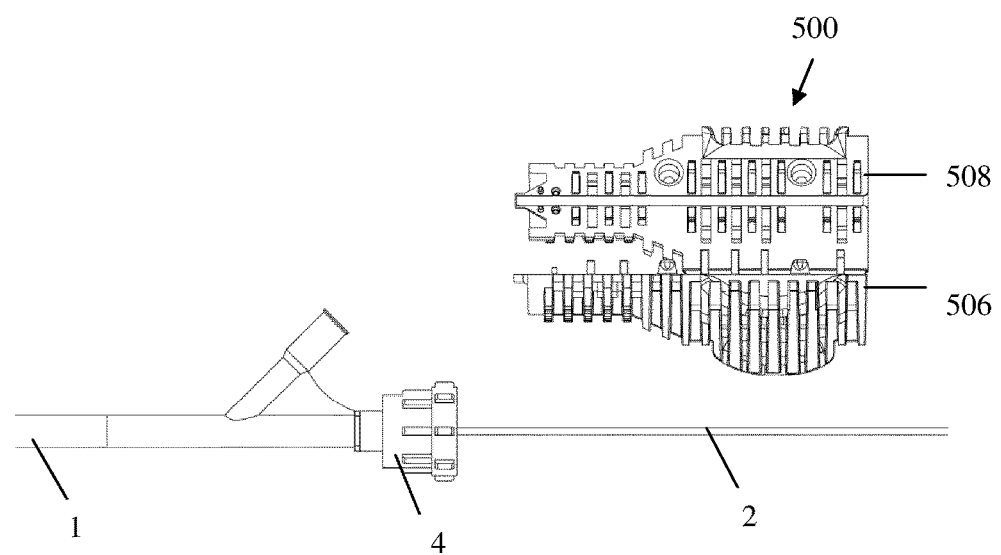
FIG. 5H is an exploded side elevational view of the thrombectomy device, the delivery catheter, and the loading device of FIG. 5A with the loading device removed from the thrombectomy device.

As shown in FIG. 5H, after the distal tip 520 is reversibly coupled to the hemostatic valve 4, the funnel 3 is advanced distally past the hemostatic valve 4 and into the lumen of the delivery catheter 1. The loading device 500 can then be retracted away from the hemostatic valve 4 and the body 502 of the loading device 500 can be opened to release and remove the loading device 500 from the shaft of the aspiration catheter 2. The funnel 3 of the aspiration catheter 2 can then be advanced to a distal portion of the delivery catheter 1 by pushing the shaft of the aspiration catheter 2 in a distal direction within the lumen of the delivery catheter 1.

FIGS. 6A-6F illustrate another embodiment of a loading device 600 for loading an expandable medical device, such as an expandable stent or funnel 3, into a delivery catheter 1. The loading device 600 shares many of the same features as described above for the loading device 500 illustrated in FIGS. 5A-5H. For example, the loading device 600 illustrated in FIGS. 6A-6F also has a body 602 that encloses a lumen 604 that is sized and shaped to receive the stent or funnel and extend from a proximal end 618 of the body 602 to a distal end 620 of the body 602. The lumen 604 can also have a diameter that is substantially constant and that is slightly greater than the diameter of the aspiration catheter 2 to which the stent or funnel 3 is attached. The lumen 604 can be cylindrical and straight and have a length that is at least as long as the stent or funnel 3 in the collapsed configuration. To access the lumen 604, the body 602 can reversibly be opened and/or separated into two portions 606, 608 to expose the lumen 604.

Here is the primary difference between the two embodiments. Instead of two portions that are equal or roughly equal halves, as shown in FIGS. 6C-6F, the first portion 606 of the body 602 is about three quarters (e.g. between about 240 degrees and 300 degrees) of a cylinder and the second portion 608 is about one quarter (e.g. between about 60 degrees and 120 degrees) of a cylinder, so that when the two portions 606, 608 are closed together the body 602 forms a complete cylinder. Another way to describe the relationship between the two portions 606, 608 is that the first portion 606 has a groove 614 that defines about three quarters (e.g. between about 240 degrees and 300 degrees) of the lumen 604 of the loading device 600 in the closed configuration, while the second portion 608 has a groove 616 that defines about one quarter (e.g. between about 60 degrees and 120 degrees) of the lumen 604 of the loading device 600 in the closed configuration. In some embodiments, the first portion 606 is about 260 degrees and the second portion 608 is about 100 degrees. The V-shaped surfaces of the first portion 606 act as an alignment feature that guides the shaft of the aspiration catheter 2 into the groove 614 as the body 602 is closed.

The remaining features can be substantially similar to the features described above in connection with FIGS. 5A-5H. For example, the body 602 of the loading device 600 has the proximal end 618 and the distal end 620 (also referred as distal tip portion) through which the lumen 604 extends. The distal tip portion 620 is sized and shaped to reversibly couple with the hemostatic valve 4 of the delivery catheter 1. When the distal tip portion 620 is coupled with the hemostatic valve 4, the lumen 604 of the loading device 600 is aligned with the lumen of the delivery catheter 1 so that the collapsed funnel 3 can be advanced from the loading device 600 and into the lumen of the delivery catheter 1.

In addition, the distal tip portion 620, when in the closed configuration, can have a cylindrical wall portion 622 that surrounds a central tubular member 624 that extends from the distal tip portion 620 from a conical projection 626. As shown, the lumen 604 extends through the central tubular member 624. This shape allows the distal tip portion 620 of the loading device 600 to tightly couple with the hemostatic valve 4 of the delivery catheter 1. In some embodiments, the central tubular member 624 extends at least partially into the lumen of the delivery catheter 1 when the distal tip portion 620 is coupled to the hemostatic valve 4. In some embodiments, the central tubular member 624 extends past the sealing mechanism of the hemostatic valve 4 when the distal tip portion 620 is coupled to the hemostatic valve 4. In other embodiments, the central tubular member 624 abuts against the end of the hemostatic valve 4 when the distal tip portion 620 is coupled to the hemostatic valve 4.

The loading device 600 described in connection with FIGS. 6A-6F can be used in a similar manner as described above for the loading device 500 illustrated in FIGS. 5A-5H.

FIGS. 7A-7C illustrate different views of another embodiment of a loading device 700 for loading an expandable medical device, such as an expandable stent or funnel 3, into a delivery catheter 1. The loading device 700 shares many of the same features and can be used in a similar manner as described above for the loading devices 500 and 600. For example, the loading device 700 illustrated in FIGS. 7A-7C also has a body 702 that encloses a lumen 704 that is sized and shaped to receive the stent or funnel 3 and extend from a proximal end 718 of the body 702 to a distal end 720 of the body 702. The lumen 704 can also have a diameter that is substantially constant and that is slightly greater than the diameter of the aspiration catheter 2 to which the stent or funnel 3 is attached. To access the lumen 704, the body 702 can reversibly be opened and/or separated into two portions 706, 708 to expose the lumen 704. In the open configuration, the inner faces 710, 712 of the two portions 706, 708 each have a groove 714, 716 that defines a portion (e.g., a half) of the lumen 704. As shown in the figures, the inner faces 710, 712 of the first and second portions 706, 708 define a plurality of alignment features 728.

The lumen 704 also extends through the distal end 720 of the body 702. The distal end 720 or distal tip portion is sized and shaped to reversibly couple with the hemostatic valve 4 of the delivery catheter 1. When the distal end 720 is coupled with the hemostatic valve 4, the lumen 704 of the loading device 700 is aligned with the lumen of the delivery catheter 1 so that the collapsed funnel 3 can be advanced from the loading device 700 and into the lumen of the delivery catheter 1. As shown in FIG. 7A, the distal end 720, when in the closed configuration, can have a cylindrical wall portion 722 that surrounds a central tubular member 724 that extends from the distal end 720 from a conical projection 726. The lumen 704 extends through the central tubular member 724. This shape allows the distal end 720 to tightly couple with the hemostatic valve 4 of the delivery catheter 1. The central tubular member 724 may extend at least partially into the lumen of the delivery catheter 1 when the distal tip portion 720 is coupled to the hemostatic valve 4. Alternatively, the central tubular member 724 may extend past the sealing mechanism of the hemostatic valve 4 when the distal end 720 is coupled to the hemostatic valve 4. Even, the central tubular member 724 may abut against the end of the hemostatic valve 4 when the distal end 720 is coupled to the hemostatic valve 4.

In some embodiments, as shown in FIG. 7B, the body 702 also includes one or more finger tabs 734 that provide surfaces for the user to press against to open and close the body 702.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A loading device for loading a medical device into a catheter, the medical device having a nonexpandable portion and an expandable portion, the latter having an expanded configuration and a collapsed configuration, the loading device comprising:
   a lumen configured to receive the expandable portion of the medical device, the lumen having a length at least as long as the expandable portion of the medical device when the expandable portion is in the collapsed configuration, the lumen having a diameter that is greater than the collapsed configuration of the medical device;
   a first body portion and a second body portion that are reversibly separable to expose the lumen in an open configuration and enclose the lumen in a closed configuration, the first body portion comprising an inner face, and the second body portion comprising an inner face, wherein the inner face of the first body portion has a first groove extending from and below the inner face of the first body portion that defines a first portion of the lumen and the inner face of the second body portion has a second groove extending from and below the inner face of the second body portion that defines a second portion of the lumen;

a first plurality of alignment features disposed around the first groove and extending from and above the inner face of the first body portion, each of the first plurality of alignment features having a receiving surface configured to guide the nonexpandable portion of the medical device into the first groove, and a first plurality of receptacles on the inner face of the second body portion that are each configured to receive an alignment feature of the first plurality of alignment features when the inner face of the first body portion abuts against the inner face of the second body portion;

a second plurality of alignment features disposed around the second groove and extending from and above the inner face of the second body portion, each of the second plurality of alignment features having a receiving surface configured to guide the nonexpandable portion of the medical device into the second groove, and a second plurality of receptacles on the inner face of the first body portion that are each configured to receive an alignment feature of the second plurality of alignment features when the inner face of the second body portion abuts against the inner face of the first body portion; and a distal tip portion that is sized, shaped, and configured to reversibly couple with a hemostatic valve of the catheter such that the lumen of the loading device is aligned with a lumen of the catheter when the distal tip portion is coupled with the hemostatic valve of the catheter, wherein the lumen of the loading device extends through the distal tip portion.

2. The loading device of claim 1, wherein the distal tip portion is formed from the first body portion and the second body portion, wherein the distal tip portion in the closed configuration comprises a cylindrical wall portion and a central tubular member, wherein the lumen of the loading device extends through the central tubular member.

3. The loading device of claim 1, wherein the lumen of the loading device has a substantially constant diameter.

4. The loading device of claim 1, wherein the distal tip portion has a length allowing the distal tip portion to extend at least partially within the hemostatic valve.

5. The loading device of claim 1, wherein the distal tip portion has a length allowing the distal tip portion to extend past a sealing mechanism in the hemostatic valve.

6. The loading device of claim 1, wherein the first groove defines half of the lumen of the loading device and the second groove defines the other half of the lumen of the loading device.

7. The loading device of claim 1, wherein the receiving surfaces of the first plurality of alignment features are sloped downwards towards the first groove.

8. The loading device of claim 1, wherein the first and second body portions are made of a translucent or clear material.

9. The loading device of claim 1, wherein a hinge connects the first body portion to the second body portion.

10. The loading device of claim 1, wherein the first body portion has a first tab that extends from the first body portion and the second body portion has a second tab that extends from the second body portion, wherein the first tab and the second tab are proximate each other when the first body portion and the second body portion are in the closed configuration, the loading device further comprising a third tab located between about 30 degrees to 120 degrees away from the first tab and a fourth tab located between about 30 degrees to 120 degrees away from the second tab.

11. A loading device for loading a medical device into a catheter, the medical device having a nonexpandable portion and an expandable portion, the latter having an expanded configuration and a collapsed configuration, the loading device comprising:

a lumen configured to receive the expandable portion of the medical device, the lumen having a length at least as long as the expandable portion of the medical device when the expandable portion is in the collapsed configuration, the lumen having a diameter that is greater than the collapsed configuration of the medical device;

a first body portion and a second body portion that are reversibly separable to expose the lumen in an open configuration and enclose the lumen in a closed configuration, the first body portion comprising an inner face, and the second body portion comprising an inner face, wherein the inner face of the first body portion has a first groove extending from and below the inner face of the first body portion that defines a first portion of the lumen and the inner face of the second body portion has a second groove extending from and below the inner face of the second body portion that defines a second portion of the lumen, wherein the first groove defines approximately three quarters of the lumen and the second groove defines approximately one quarter of the lumen;

a plurality of alignment features disposed around the first groove and extending from and above the inner face of the first body portion, each of the alignment features having a receiving surface configured to guide the nonexpandable portion of the medical device into the first groove, and a plurality of receptacles on the inner face of the second body portion that are each configured to receive an alignment feature when the inner face of the first body portion abuts against the inner face of the second body portion; and a distal tip portion that is sized, shaped, and configured to reversibly couple with a hemostatic valve of the catheter such that the lumen of the loading device is aligned with a lumen of the catheter when the distal tip portion is coupled with the hemostatic valve of the catheter, wherein the lumen of the loading device extends through the distal tip portion.

12. A loading device for loading a medical device into a catheter, the medical device having a nonexpandable portion and an expandable portion, the latter having an expanded configuration and a collapsed configuration, the loading device comprising:

a body having a lumen configured to receive the expandable portion of the medical device, the lumen having a length at least as long as the expandable portion of the medical device when the expandable portion is in the collapsed configuration, the lumen having a diameter that is greater than the collapsed configuration of the medical device, the body comprising a first portion and a second portion that are reversibly separable to expose the lumen in an open configuration and enclose the lumen in a closed configuration, the first portion comprising an inner face, and the second portion comprising an inner face, wherein the inner face of the first portion has a first groove that defines a first portion of the lumen and the inner face of the second portion has a second groove that defines a second portion of the lumen;

wherein the body has a distal tip portion that is sized, shaped, and configured to reversibly couple with a hemostatic valve of the catheter such that the lumen of the loading device is aligned with a lumen of the catheter when the distal tip portion is coupled with the hemostatic valve of the catheter, wherein the lumen of the loading device extends through the distal tip portion;

further comprising a plurality of alignment features disposed around the first groove and extending from the inner face of the first portion and a plurality of receptacles on the inner face of the second portion that are configured to receive the plurality of alignment features when the inner face of the first portion abuts against the inner face of the second portion, wherein the alignment features around the first groove each has a receiving surface configured to guide the nonexpandable portion of the medical device into the first groove; and further comprising a plurality of alignment features disposed around the second groove and extending from the inner face of the second portion and a plurality of receptacles on the inner face of the first portion that are configured to receive the plurality of alignment features around the second groove when the inner face of the second portion abuts against the inner face of the first portion, wherein the alignment features around the second groove each has a receiving surface configured to guide the nonexpandable portion of the medical device into the second groove.

13. The loading device of claim 12, wherein the distal tip portion is formed from the first portion and the second portion, wherein the distal tip portion in the closed configuration comprises a cylindrical wall portion and a central tubular member, wherein the lumen of the loading device extends through the central tubular member.

14. The loading device of claim 12, wherein the distal tip portion has a length allowing the distal tip portion to extend at least partially within the hemostatic valve.

15. The loading device of claim 12, wherein the distal tip portion has a length allowing the distal tip portion to extend past a sealing mechanism in the hemostatic valve.

16. The loading device of claim 12, wherein the first groove defines half of the lumen of the loading device and the second groove defines the other half of the lumen of the loading device.

* * * * *